United States Patent
Genovese et al.

(10) Patent No.: US 6,228,657 B1
(45) Date of Patent: May 8, 2001

(54) ENVIRONMENTAL MATERIAL TICKET READER AND AIRBORNE HAZARD DETECTION SYSTEM

(75) Inventors: James A. Genovese, Street; Patrick M. Nolan, Havre de Grace, both of MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/387,875

(22) Filed: Sep. 1, 1999

Related U.S. Application Data

(60) Provisional application No. 60/102,144, filed on Sep. 29, 1998.

(51) Int. Cl.[7] .................................................. G01N 31/00
(52) U.S. Cl. ..................... 436/167; 436/164; 436/165; 436/181; 436/104; 422/61; 422/82.05; 422/83; 422/86; 422/87; 422/88; 422/91; 73/23.2
(58) Field of Search ................................. 422/55, 50, 56, 422/58, 61, 69, 68.1, 71, 82.05, 83, 85, 86, 87, 88, 91; 436/159, 104, 167, 181, 164–165; 73/23.2

(56) References Cited

U.S. PATENT DOCUMENTS

| | | | |
|---|---|---|---|
| 3,628,915 | * 12/1971 | Robertson | 23/230 R |
| 4,269,804 | * 5/1981 | Kring | 422/86 |
| 4,336,337 | * 6/1982 | Wallis et al. | 435/292 |
| 4,428,907 | * 1/1984 | Heijenga et al. | 422/61 |
| 4,913,881 | * 4/1990 | Evers | 422/56 |
| 4,918,025 | * 4/1990 | Grenner | 436/165 |
| 5,035,860 | * 7/1991 | Kleingeld et al. | 422/61 |
| 5,281,395 | * 1/1994 | Markar et al. | 422/82.05 |
| 5,328,847 | * 7/1994 | Case et al. | 435/291 |
| 5,837,546 | * 11/1998 | Allen et al. | 436/169 |
| 5,874,046 | * 2/1999 | Megerle | 422/68.1 |
| 5,935,862 | * 8/1999 | Novak | 436/104 |
| 5,993,743 | * 11/1999 | Nordman et al. | 422/94 |

* cited by examiner

*Primary Examiner*—Jill Warden
*Assistant Examiner*—Kathryn Bex
(74) *Attorney, Agent, or Firm*—Ulysses John Biffoni; Vincent J. Ranucci

(57) ABSTRACT

An airborne hazardous material reader device capable of receiving a collection element. The reader device has a body forming a slot area for receiving the collection element. The body has a crushing mechanism located within the slot area for breaking ampules attached to the collection element containing chemical testing reagents, a micro-pump positioned proximate to the slot area for controlling the temperature next to the collection element, a diode reading component incorporated within the body for distinguishing color changes from the release of chemical testing reagents from the broken ampules, an indicator for indicating the presence of a hazardous material when the diode reading component distinguishes color changes and a microprocessor that coordinates the sequence of the reader device. A method for airborne hazardous material detection also is disclosed.

16 Claims, 1 Drawing Sheet

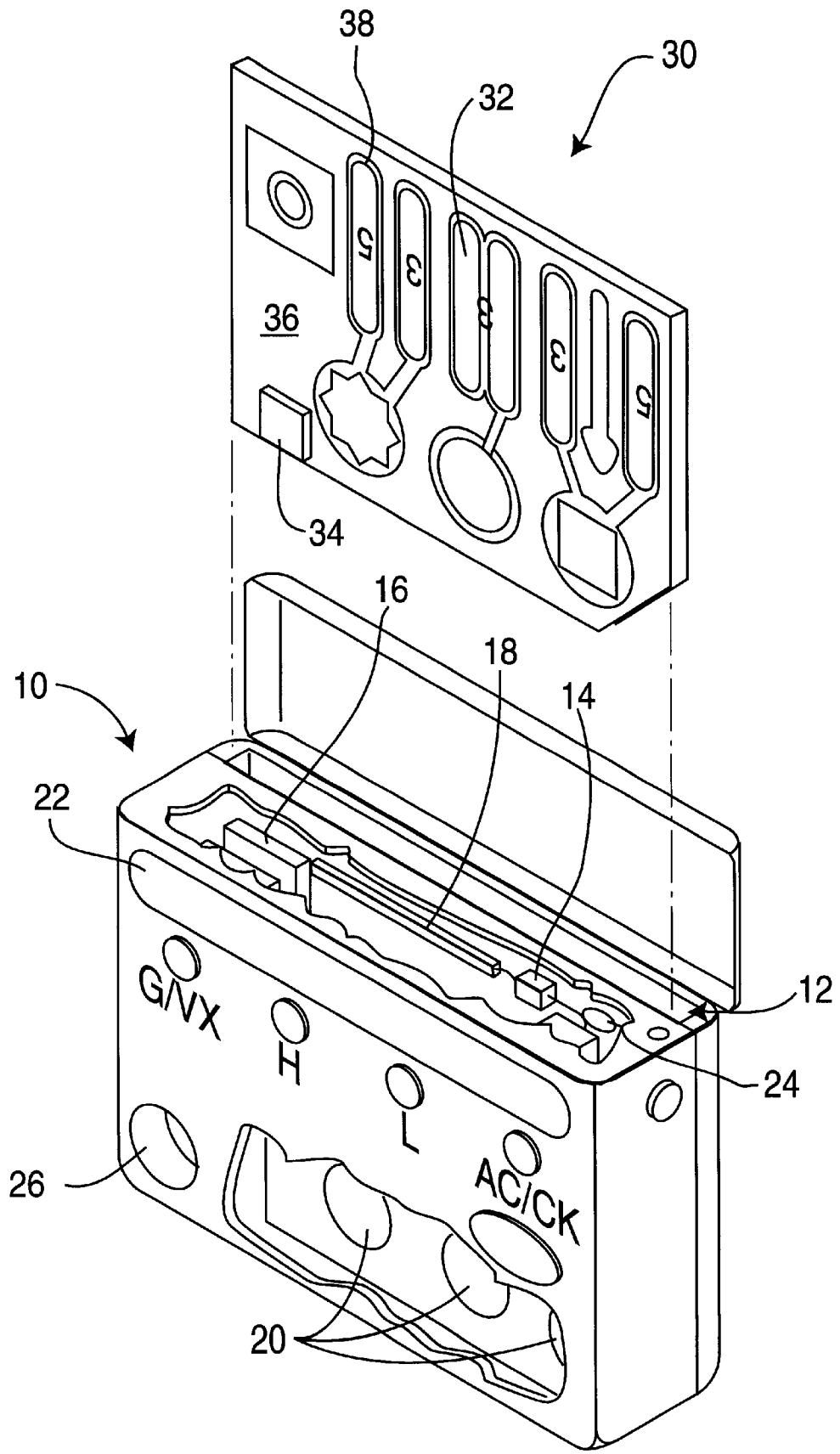

ENVIRONMENTAL MATERIAL TICKET READER AND AIRBORNE HAZARD DETECTION SYSTEM

This patent application is a nonprovisional continuation of provisional application Ser. No. 60/102,144 filed on Sep. 29, 1998.

GOVERNMENT INTEREST

The invention described herein may be manufactured, licensed, and used by or for the U.S. Government.

BACKGROUND OF THE INVENTION

1. Field of the Invention

The present invention relates to a reader device for collection elements. More particularly, the reader device automatically reads collection elements for determining the presence of hazardous material, such as biological and chemical agents. The reader device of the present invention may be used with a modified M256 ticket or other types of collection elements.

2. Description of the Related Art

Manipulating and interpreting hazardous material detection equipment becomes problematic during field operations. Cumbersome protective gear, in combination with working in a hazardous environment, interferes with the proper use of detection equipment. Over the past 40 years, advances in detector wet chemistry and ergonomic design, aiding in the human interface with the detectors, has occurred. The United States Department of Defense, specifically the Army, has developed and improved the detection of chemical agents in the vapor phase. Enzymatic methods have been incorporated into chemical agent detection kits starting with the AN-M15A1 and AN-M15A2 through the experimental design XM1189 and into the current configuration, the M256 chemical agent detection kit. The evolution of the chemical agent detection kit was caused by changing operational requirements of improved sensitivity, reliability, and operational use. The improvements were based on an improved operational knowledge base and by applying evolving technological advances in chemistry, engineered materials, and engineering production. In 1963 the M256 chemical agent detection kit configuration resulted from a reevaluation to simplify standardized chemical detection kits to meet operational field requirements. Since the development of the M256 chemical agent detection kit, several developments have occurred in the chemical threat to military units. Additionally, an emerging chemical agent terrorist threat in the civilian sector is escalating at a rapid rate resulting from changing world politics, technology availability, and the proliferation and easy access of information related to toxic chemical substances. However, with the larger number of threatened locations, the military and civilian communities have difficulty in providing the personnel assets required to contend with the large-scale potential threat of a terrorist or other types of chemical agent incidents.

Emergency responders, such as hazardous material technicians, firefighters, emergency medical technicians, have the primary mission of confirming the identity of hazardous materials as quickly as possible, as mandated by standard operating procedures (Occupational Safety and Health Act (OSHA) standard 29 CFR 1910.120). The M256 chemical agent detection kit is capable of detecting a variety of chemical warfare agents, such as nerve (G-Class, V-Class), blister (mustard (H, HD), phosgene oxime (CX), Lewishe (L), and blood (hydrogen cyanide (AC), cyanogen chloride (CK)), at concentrations below those Immediately Dangerous to Life and Health, (IDLH) as defined by the National Institute for Occupational Safety and Health (NIOSH).

Although the M256 chemical agent detection kit provides an affordable, reliable and prompt chemical detector that is available to most military units and civilian communities, it is labor intensive. Operationally, the M256 may require two operators, one to perform the chemical testing and the other to read the instructions. Operators of the M256 chemical agent detection kit must follow detailed and precise instructions involving many physical and mechanical manipulations in a set chronological sequence. Generally, operators must conduct the chemical detection process while in protective clothing; with civilians using the Personal Protective Equipment (PPE), Level A and the military personnel using the Military Operational Protective Posture (MOPP), Level IV. In both military and civilian protective gear, the operator's ability to perform tasks is severely reduced. The clothing restricts physical movement of any kind, e.g., arm motion, both range and speed with resistance. Temperature buildup from the adiabatic nature of the clothing, i.e., poor heat transfer processes, causes physical and psychological stress, as well. Respiratory protection exacts a physical and psychological penalty, including a restriction of natural breathing. Additionally, peripheral and direct vision is impaired in range, depth, and clarity due to the eye protection incorporated into the facial mask and the extra face shield with the overgarment in the Level A suite. Impaired vision exacerbates the existing difficulty in reading the instructions set on the packaging material of the M256 chemical agent detection kit, with the instructions printed in small 8 point font lettering, small illustrations, and non-distinctive color contrast of light green lettering on olive drab green background. Collectively, these factors significantly encumber the operator's ability to perform any chemical detection task. Moreover, operators confined in Level A PPE have a limited clean air supply from a Self Contained Breathing Apparatus (SCBA), circa 10 minutes to 40 minutes, depending on air consumption rates, with the high physical and mental stress environment of a chemical threat emergency situation generally limiting the time. Typically, current hazardous material teams have highly trained but limited personnel resources, which can be consumed to perform the operations required by the M256 chemical agent kit.

The M256 chemical agent detection kits possesses several drawbacks for use in military field operations. Several factors lead to variations in detection results of the M256. There is limited environmental control allowing a broad range of temperature conditions to affect the detection kit. Ultraviolet (UV) radiation from sunlight and ambient temperature ranging from desert temperatures to arctic conditions influence the chemical kinetic rate of reaction, causing variation in the rate and intensity of the calorimeter development which indicates the presence of chemical warfare agents. Air sampling may not be uniform depending on the location of the chemical agent source, the location of the detection kit, the relative wind vector, and orientation of the detection kit sampling surface. Temperature control on the blister agent detection area from the exothermic reaction is not well controlled to ensure reproducibility. Additionally variations occur from person to person in color and intensity interpretation.

There is a need for airborne hazardous material detection beyond that permitted by the capability of the M256, and to simplify procedures in testing for the presence of hazardous materials, such as chemical agents.

SUMMARY OF THE INVENTION

In view of the foregoing, it is therefore an object of the present invention to provide a device that provides a simplified mechanism for testing for the presence of hazardous materials.

It is further an object of the present invention to provide a device that increases the capability of currently available detection methods to detect the presence of hazardous materials.

These and other objects are achieved by the present invention which includes an airborne hazardous material reader device, comprising a body forming a slot area capable of receiving a collection element therein, a crushing mechanism located within the slot area capable of breaking ampules attached to a collection element sufficient to release chemical testing reagents therefrom, a micro-pump positioned proximate to the slot area and capable of moving hazardous material into slot area, a temperature control assembly capable of thermally regulating the temperature within the slot area, a diode reading component incorporated within the body, the diode reading component capable of distinguishing color changes on a received collection element, an indicator means effective to indicate the presence of a hazardous material when the diode reading component distinguishes color changes, and, a microprocessor incorporated into the body capable of activating the crushing mechanism, micro-pump, temperature control assembly and diode reading component in a predetermined sequence and initiating the indicator at predetermined color changes.

The present invention further includes an airborne hazardous material collection element, comprising a porous substrate capable of absorbing airborne contaminants thereon, and, ampules containing chemical reagent material attached to the porous substrate and capable of breakage that releases the chemical reagent material onto the porous substrate, wherein the collection element is capable of insertion into a reader device.

Additionally, the present invention includes a method for airborne hazardous material detection, comprising the steps of providing an airborne hazardous material reader device, comprising a body forming a slot area capable of receiving a collection element therein, a crushing mechanism located within the slot area capable of breaking ampules attached to a collection element sufficient to release chemical testing reagents therefrom, a micro-pump positioned proximate to the slot area and capable of moving hazardous material into the slot area, a temperature control assembly capable of thermally regulating the temperature within the slot area, a diode reading component incorporated within the body, the diode reading component capable of distinguishing color changes on a received collection element, an indicator means effective to indicate the presence of a hazardous material when the diode reading component distinguishes color changes, and, a microprocessor incorporated into the body capable of activating the crushing mechanism, micro-pump, temperature control assembly and diode reading component in a predetermined sequence and initiating the indicator at predetermined color changes; placing a collection element into the reading device; transporting the reading device containing the collection element to an area of possible contaminants; and, inserting a collection element into the reader device, wherein the microprocessor regulates the temperature of the area adjacent to the collection element and activates the crushing mechanism to crush ampules attached to the collection element to release a first chemical reagent. Additionally, the method may include that the microprocessor initiates the micro-pump to collect airborne hazardous material, activates the crushing mechanism to crush ampules attached to the collection element to release a second chemical reagent, initiates a time-interval color reading of the collection element by the diode reading component, and activates the indicator means in relation to the color reading of the diode reading component.

BRIEF DESCRIPTION OF DRAWINGS

FIG. 1 illustrates a perspective view of the reader device and insertable collection element of the present invention.

DETAILED DESCRIPTION OF THE PREFERRED EMBODIMENT

The present invention is a reader device and collection element for detecting the presence of airborne hazardous materials. The reader device, referred to as the Environmental Material Ticket Reader (EMTR), is designed to automatically read all forms of the collection element, referred to as the Environmental Material Tickets (EMTs). Additionally, the reader device may be used with collection elements comprising modified M256 tickets and environmental samplers.

Airborne hazardous material include chemical and/or biological agents that are hazardous to living beings in an environment. The agents generally include, but are not limited to, agents known as chemical and/or biological warfare agents used to inflict casualties on military units and/or civilian communities, and other types of toxic compounds, such as naturally occurring diseases, toxic vapors spewed into the atmosphere from volcanic eruptions, gas leaks, and other such occurrences that cause harmful chemical and/or biological compounds to be present in an environment. The hazardous materials may be present in an environment from a terrorist attack, military operation, accidental release, and/or other like discharges that place a dangerous substance in close proximity with living beings, particularly humans.

Collection Elements

As seen in FIG. 1, collection elements 30 of the present invention include a porous substrate 36 for the collection of airborne hazardous materials, chemical reagents 32 for analyzing or preserving the collected hazardous materials, and an initiator key 34 that are insertable into a reader device 10. Additionally, the collection elements 30 may include modified M256 chemical agent kit tickets and TRAINS M28/29 training tickets, that are modified by removing the heater assembly, protective strip, Lewisite tab #1, and/or Lewisite tab #2, or that are initially manufactured without these components. The collection element 30 provides a simpler employment and more timely deployment in the reader device 10 than the current M256 ticket and M28/29 tickets in their respective detection devices. In addition to lowering production costs, the modified M256 tickets facilitate the insertion of these collection elements 30 into the reader device 10 by reducing preparation time. Less steps are needed for employment with the reader device 10, and fewer errors in collection element 30 preparation occur than with previous tickets. The elimination of the heater assembly, for example, removes certain environmental disposal problems, reduces the potential for skin burns from the chemical heater, and eliminates the fire ignition source and the inhalation hazards associated with the gas producing the thermal reaction. The heater assembly is removed also to minimize contamination of detector areas. Removal of the heater assembly and protective strips is accomplished with the steps of: placing the M256 ticket with ampule top tips facing down into the center of hand, grasping the M256 ticket with the fingers on one side and the palm on the other side, with caution not to accidentally crush the ampules.

Additionally, the collection element 30 may be configured to detect vapor phase and aerosol phase (liquid or solid) chemical or biological materials of interest, non-exclusive examples including, e.g., oxygen, chlorine, fluorine, ammonia, methane, ethane, propane, butane, hydrocarbons vapors, and/or other toxic or potentially dangerous liquid or solid chemical aerosol. Biological materials in the aerosol phase include, but not limited to, *Bacillus anthracis, Yersinia pestis,* Staphylococcus Enterotoxin B, *Clostridium botulinum,* Ricin, *Coxiella burnetii, Francisella tularensis,* Venezuelan Equine Encephatitis virus, variola virus, tuberculosis, and viral hemorrhagic fevers (Yellow, Ebola, Marburg, Lassa, Rift Valley, and Dengue).

The collection elements 30 may include a preservation function when used in the reader device. In this form the collection elements 30, referred to as Environmental Material Collection Tickets (EMCTs) serve as sample collectors for analysis at a remote or on-site laboratory. The EMCTs serve as an environmental sampler, analyzing for a broad spectrum of vapor and/or aerosol airborne chemical and/or biological environmental materials. The EMCTs used in conjunction with the reader device 10 effectively collect and preserve the aerosol or vapor airborne chemical or biological samples in a manner that is capable of being time-sequenced. The EMCT collection elements 30 are fabricated with a re-sealable forensic sampling envelope. The integrity of a used collection element 30 is maintained with the use of these re-sealable forensic sampling envelopes. The envelope reduces permeation of the contained hazards, cross contamination, and affords a more facile logging and transfer of these collection elements 30 for future analysis. EMCTs may be used to collect forensic evidence or other types of analysis, generally according to specific organizational standard operational procedures (SOPs). This affords the operator the ability to collect and save vaporous or gaseous material that is analyzed and identified by more comprehensive analytic techniques available in a laboratory, e.g., GC, GC/MS, IR, UV, AE, AA, IC HPLC, etc. EMCTs utilize crushable vials with a plastic liquid channel to direct the specific reagent 32 to the detection area that improves collection efficiencies, sample stability, sample viability, and sample preservation for both chemical and biological materials. The EMCT form of the collection element 30 has the same form as the EMT, but has strips of adsorbent material included. The strips of adsorbent material non-exclusively include charcoal, zeolites, resins, paper materials, polymeric materials, and other such materials that act as stationary solid-phase collectors. The material composition of the adsorbent strip may be a single component, or multiple components to accommodate various absorption affinities of the various vaporous airborne materials. The adsorbent strips are located on the collection element 30 as to maximize the surface contact area of the reader device 10 baffling/plenum. Preferably, the adsorbent material is positioned along the left-hand side and bottom edge of the collection element 30. The collection element 30 backing material can be constructed of a suitable support material, such as paper or polymeric material composition. Additionally, the collection element 30 backing material may act as the absorbent material to simplify production processes and associated costs. Both the EMT and EMCT collection elements 30 may be designed to process multiple samples of similar or dissimilar airborne materials simultaneously, multiple samples of similar airborne entities at different times throughout the sampling process, or multiple samples of dissimilar airborne entities at different times throughout the sampling process. Generally, the EMT has two distinct chemical reagents 32 for processing the hazardous materials, and the EMCT has a single chemical reagent 32, however, the type and number of chemical reagents 32 for the EMT and EMCT vary according to a given use, with the type and number of chemical reagents 32 being determinable by those skilled in the art.

Each collection element 30 has an element identification marker, permitting visual inspect of the collection element 30 to ascertain the collection element's capabilities. The initiator key 34, such as a color key code swatch, alphanumeric indicators for optical character reader (OCR) capable systems, or bar codes, enables the reader device 10 to automatically identify the process to be conducted. Preferably, the collection elements 30 have a notch on the low right-hand corner to preclude incorrect insertion of the collection element 30 into the reader device. As a unitary component, the possibility of the collection element, without loose paper or rivets, interfering with reader device 10 functioning is greatly reduced.

The EMCT includes strips of particulate adsorbent material, such as the non-limiting examples of agar, adhesives, resins, aerosol gel materials and high surface area macro-porous materials, to act as a stationary solid-phase collector. Another embodiment includes the glass ampules 38 encased in transparent, flexible plastic casing with conduits that lead to the collection area on the collection elements 30. The ampules 38 may contain various materials to increase sampling efficiencies and sample stability, for chemical and biological airborne entities. The individual materials may vary in composition to increase viability, culturability, and incubation of a particular biological entity or the suppression of viability, culturability, and incubation of a particular entity. The factor regarding viability or lack thereof, includes but not limited to, humidity, nutrients, wettability/solubility, bactericides, and fungicides. The chemical reagents 32 contained in the ampules 38 may be temporally and spatially distributed to achieve a particular processing sequence. The same chemical reagent 32 in the ampules 38 may also be included, or pre-loaded, on the collection area substrate 36. Additionally, temperature control of the collection media may be accomplished by the heating/cooling surface (Peltier Device) located near the collection surfaces, describe below.

The material composition of the adsorbent strip may be a single component or multiple components to accommodate various particulate absorption dynamics, such as size, bounce factor, and wettability of the various airborne particulate or aerosol materials. The particulate adsorbent strips are located on the collection element 30 as to maximize the surface contact area and inertial impaction dynamics of the reader device 10 baffling/plenum. The adsorbent material is positioned along the left-hand side and bottom edge of the collection element 30, with the backing material and/or substrate 36 constructed of paper, polymeric and/or other suitable material.

The collection elements 30 may be configured with discrete chemistries so that a broad spectrum of other airborne environmental materials are detected and/or collected. For example, when used with the reader device 10, both aerosol and vapor samples may be analyzed. Environmental airborne contaminants may be either chemical or biological in nature.

The collection elements 30 use the simplicity and efficiency of crushable vials to assist in sample collection, analysis and preservation. Crushable vials are particulary useful to identify and sample bio-molecules. Collection elements 30 are formed for the specific use with the reader device 10 of the present invention. Together, the reader device 10 and collection elements 30 are a system, where the collection element 30 is a removable component that is automatically prepared and read when inserted into the reader device 10. The collection elements 30 also include a generic class of chemistries for the detection, collection, stabilization, and sample preparation of airborne chemical and biological entities. Additionally, the collection elements 30 may be manipulated and read manually, when desired. The collection elements 30 may be manipulated sequentially to provide increasing detailed analysis of a chemical agent threat, by providing information from a generalized compound class to a more detailed class identification. By way of example, a first detection provides an analysis determining a chemical verses biological class. If a chemical class is confirmed, a second identification level determining a nerve agents verses blister agents verses blood agents verses choking agents follows. With the confirmation of a nerve agent, classification of the type of nerve agents follows, i.e., organophosphonates verses carbamates. With the confirmation of an organophosphonates class, the determination of the type of organophosphonate may follow, e.g., GA, GB, GD, GF, VX. Additionally, specific components may be evaluated as a function of time. The classification process using information content layers may be performed on individual collection elements 30 sequentially, or combined on a single collection element 30.

Reader Device

The reader device 10 of the present invention automates the collection element 30 sampling and development processing. The operator first turns on the reader device 10 via an "on/off" switch located in a position distinct from the "start/reset" button. The "on/off" switch is easily operated by an operator in heavy protective gloves using a relatively large button or switch. When initially turned on, a microprocessor 24 in the reader device 10 warms-up and performs a systems check on the reader device 10, such as internal checks of temperature, CPU, memory, and optical component checks of detector elements, lights source, light path, and background scale check between zeroing and 100% scale, date, time and battery condition, while the operator proceeds with other tasks, such as collection element 30 selection. After a systems check, the reader device 10 registers a "ready mode". The collection element 30, for example a modified 256, is removed from its packaging. Preferably, the collection element 30 is loaded into the reader device 10 prior to entering a hazardous material incident, such as having one person prepare the collection element 30 and another person suiting up in protective gear to enter a "hot zone" of hazardous material contamination. For M256 tickets that are modified on-site, the initiator key 34 may be placed on the ticket and the heater assemblies are individually crushed and allowed to cool to a safe disposal temperature, at which time they are discarded in an appropriate manner. Generally, eye protection, protective cloth and chemical and thermal resistant gloves are used at all times during the process. Both halves of the white paper detector tab #2 are rubbed on the tablet, after which the operator opens the top cover of a slot area 12 in the reader device 10 and inserts the collection element 30 into the reader device 10. The top cover closes automatically, via a spring loaned mechanism. The microprocessor 24 initializes the detection process of the reader device 10 by reading the initiator key 34 on the collection element 30. Alternatively, the white paper detector tab #2 is removed and then inserted into the reader device. The reader device 10 is maintained in a upright position, as the chemical reagents 32 from the broken ampules 38 are located above the detector areas and provide a gravity feed of the chemical reagents 32. An interlock switch, preferably mercury level switch, ensures that the reader device 10 maintain an upright and level position before the reader device 10 allows the operator to start the automated loading process. Additionally an alarm is activated should the reader device 10 accidentally fall before all of the ampules 38 are broken, and allotting an appropriate amount of time for the liquid chemical reagent 32 to adsorb into the detector area substrate 36. The optical component for the detection of Lewisite is placed inside the reader device 10 directly over the Lewisite tablet, with the top of the Lewisite detection tablet directly monitored for a color change, such as from brown to green.

The notch cut out of the collection element 30 in the low right-hand corner, preferably by having a small 45 degree angle piece removed, interferes with a reader device 10 notch block located at the bottom in the right-hand corner if the operator accidentally places the collection element 30 in the wrong way, such as upside down or the right-side on the left. When the collection element 30 is placed in the reader device 10 incorrectly, the collection element 30 does not seat at the bottom of the reader device 10. Subsequently, the top cover is unable to close and the interlock switch, located in between the bottom of the top cover and top of the top collection element 30 holder opening, remains in the open position. Likewise, when the top cover does not close properly for any other reason, e.g., an obstruction between top cover and the top of the reader device 10 preventing the collection element 30 not to properly seat, the reader device 10 does not allow process to continue because of the open position of the interlock switch. The interlock mechanism prevents foreign object debris from obstructing or diverting the proper air flow conditions, sensor and collection element 30 area alignment, and heater alignment, or stray light from entering in from the top of the reader device 10 slot area 12.

The reader device 10 then checks the temperature of the liquid chemical reagents 32 on the collection element 30 using a thermocouple, or perform a heating process for a pre-set time interval. This ensures that chemical reagents 32 remain non-frozen in a liquid phase, and that the chemical kinetic reaction will proceed at a reproducible and/or acceptable rate. Additionally, temperatures below ambient may require long chemical reaction rates and yield false results. After the collection element 30 achieves an acceptable temperature, the reader device 10 evaluates the collection element's physical condition, such as checking for white clean detector areas to ensure that collection elements 30 have not been contaminated with dirt, and that the ampules 38 remain unbroken.

The reader device 10 accommodates collection elements 30 comprising modified M256A1 tickets and the modified TRAINS M28/29 tickets. The collection elements 30 are manufactured and packaged without the Lewisite tab #1, Lewisite white paper tab #2, heater assembly, and the protective strip. Additionally, the initiator key 34 is placed on tickets. As such, the collection element 30 are ready to insert into the reader device 10.

Once the collection element 30 and reader device 10 are deemed operational, the collection element 30 is processed according to the instructions to the microprocessor 24 keyed by the initiator key 34. The glass ampules 38 are cracked/broken in the appropriate sequence and the appropriate time with a crushing mechanism 16 within the reader device 10. The glass ampules 38 are broken with physical contact with a hard surface. The hard surface crushing mechanism 16 may be powered by a spring, battery, or other type of cracking motion, determinable by those skilled in the art. Preferably, a solenoid is used for impelling the hard surface to crack the ampules 38. The timing sequence and detector area reading sequence may vary between different collection elements 30 or different environmental conditions. Additionally, the reader device 10 improves rates of the physical processes, compared to the M256 as processing conditions are controllable, e.g., drying time of the blister agent, continuous reading from a physically stationary reader device, and/or improved hazardous material collection in a concentrated form, described below.

A temperature control assembly 18 thermally regulates the temperature within the slot area 12. A heating device, such as a Peltier or resistive type, is located near a detection area on the collection element 30, for example, a blister agent detector area, to accelerate the chemical reagent 32 evaporation process. Cooling devices, such as a Peltier, may be placed physically near other collection element 30 detection areas to retard the evaporation rate, when needed. The heating device provides a uniform heating of the area around an inserted collection element, and zone heating for processing the chemical reagents 32 with the hazardous materials. The heating devices, and/or cooling devices, are connected, via the microprocessor 24, with a thermocouple, or other similar regulating device to form the temperature control assembly 18.

Exterior air from outside of the reader device, moves across the detector area pushed by the micro-pump 14 comprising a fan/blower mechanism and/or baffling/plenum to increase the concentration of the hazardous material over a given unit time. The micro-pump 14 increases the time to detection by delivering more vaporous agent to the detector per unit time. The overall sensitivity is increased from more vaporous chemical agent concentration being delivered per unit to the detection areas on the collection element 30. The improved convective mass transport also shortens the chemical reagent 32 evaporation time specifically for the blister agent detector area by decreasing the concentration gradient of reagent vapor. A concentrator may also be added to the intake port when increased sensitivity is desired. The fan/blower flow rate and baffling/plenum dimensional designs are adjusted to yield the optimal flow conditions and residence time over the detector area, with the adjustments determinable by those skilled in the art. Since the height and length are fixed plenum dimensions, with respect to the collection element 30 detection area, the width may be adjusted accordingly. The greater the width of the baffling/plenum, the longer the mean diffusion time of the reactant chemical reagents 32, which is further away from the detector area surface. The flow rate is adjusted so that the mean diffusion time is shorter and the residence time of the detector area surface is increased. The direction of flow through the plenum remains important. The air intake is located on top near and before the detection area of the Lewisite strip and exhausts near the blister agent detection area. This minimizes contamination of the nerve agent and blood agent detection areas from the evolving reagent vapor of the blister agent detection area, which is a known interference.

As the air mass moves over the detector areas on the collection element 30 as a function of time, the color changes, i.e., hazardous materials react with the chemical reagents 32, that is measured at a specific wavelength or wavelengths for each detector area corresponding to the unreacted color and the reacted color. A diode reading component 20 comprising diodes provides a photometric assessment in visible, ultraviolet, infrared, and/or other light wavelengths for analysis. The reader device 10 measures the wavelength(s) and relative intensities of the reflected light from the surface of the detection area. The diode reading component 20 may automatically read a rate of color change and/or color intensity as a function of time to provide an indication of hazardous material concentration, and to provide an earlier alarming and warning capability. The reader device 10 increases reproducibility and reliability by quantitatively measuring the color wavelength and intensity. Since concentration affects the rate of a chemical reaction, it is possible to obtain the vaporous agent concentration by monitoring the color intensity as a function of time.

For the reflectance version of the diode reading component 20, the light source is polychromatic in nature, such as an incandescent lamp, plasma fluorescent lamp or LED. The light source is directionally oriented orthogonal to the plain of the collection element 30 and placed near the collection element 30 detection area surface. Three light detection diodes, or Charged Coupled Device (CCD), that are red, green and blue wavelength sensitive, are directionally oriented orthogonal to the plain of the collection element 30 and placed just aft of the shielded white light source to minimize detection of stray light emissions. For the transmission version of the optical component the polychromatic light source is located behind the detection area. Each detection element is located over all four detection areas. For Lewisite detection, two possible configurations exist. One configuration reads the white paper Lewi site tab #2 and has the detection element oriented in the upward direction. In the other configuration, the detection element is oriented orthogonal to the direction of the collection element 30 and is placed directly over the Lewisite tablet.

Another diode reading component 20 version employs a light collimator attach to an optical fiber leading to another light diffuser placed directly in front of a three color, red, blue, green (RBG), detector diode or CCD detector element. The light collimator is placed orthogonal to the collection element 30 detection area surface, but behind the emitting light source to minimize stray light scattering from the light source and nearby structural surfaces. This configuration has one detector element with four fiber optics leading to it. All optical components are constructed from a suitable material, such as glass or plastic.

The structural surfaces of the optical cavity is coated with flat black, non-fluorescing material to minimized surface reflection and surface scattering. The three color light intensities are measured and processed to determine the color and intensity of the surface of the detection area. When the color and intensity matches a pre-defined value, a determination of an indicator/alarm state is issued for all four detection areas.

The light source and detector element of the diode reading component 20 may include reflective and direct light from sources and detector elements such as single or multiple polychromatic light source, single or multiple detector(s), mirrors, band pass or cutoff filter, fiber optics, prism, holographic grading, and/or combination thereof, with the arrangement determinable by those skilled in the art.

When the collection elements 30 are used as a chemical vapor/gas sample collector and a particulate sample collector, the microprocessor 24 has an automated variable start time and a variable sampling duration capability. Multiple reader devices 10 may be employed using various delayed start times to cover a specific time interval at a particular location. The microprocessor 24 identifies the type of collection element 30 inserted by the initiator key 34, such as a color coded swatch area located on the middle left-hand side of the collection element 30 and in between the Lewisite tablet and detector area, for example, white for the modified M256 and M28/29 tickets, and other colors for other types of collection elements 30. The chemical vapor/gas collection mode requires the insertion of the vapor collection form of the collection element 30.

The reader device 10, in addition to the chemical vapor/gas collector, can collect liquid or solid phase chemical and biological particulates or aerosols. This affords the operator the ability to collect vaporous or gaseous material so that it can be saved, analyzed and identified by various analytic techniques at an on-site or remote laboratory, e.g., PCR, ELISA, antigen/antibodies analysis, DNA Probes, FC, GC, GC/MS, IR, UV, AE, AA, IC, HPLC, etc., generally in compliance with applicable procedures for a given protocol, such as specific analytic techniques for forensic evidence. When using an automated variable start time collection element, multiple reader devices 10 may be employed using various delayed start times to cover a specific time interval at a particular location.

The reader device 10 may also function with existing TRAINS (M28/29) training tickets for testing the reliability of the reader device 10.

The reader device 10 provides minimal operator participation, short startup time to expedite data acquisition process, simple operation instructions to reduce detection processing errors, easy manipulations to conduct the procedure (especially in PPE or MOPP), temperature controlled during sampling process for improved reproducibility and reliability, temperature controlled during development process for improved reproducibility and reliability, UV radiation controlled for improved reproducibility and reliability, temperature control for blister agent test for improved reproducibility and reliability, improved heat transfer rate for blister agent test to shorten chemical reagent 32 evaporation time, improved convective mass transport to shorten reagent evaporation time, i.e., remove/reduce vapor concentration of reagent over detector surface, quantitative interpretation in color (wavelength of light), quantitative interpretation in color intensity, increased performance, higher sample air volume over detector area to improve convective mass transport, continuous detector reading, i.e., monitor collection element 30 development, variable start times affording continuous air sampling as a function of time for multiple units, automated sampling procedure, automated development procedure, automated warning, automated reporting, temperature profile is maintained while sampling, increased reproducibility, controlled flow volume over detector area for improved reproducibility and reliability, controlled timing on development process for improved reproducibility and reliability, works with the TRAINS M28/29 tickets for training purposes, works with the TRAINS M28/29 tickets for calibration purposes, works with the modified M256A1 tickets, works with the modified M28/29 training tickets, automated vapor sampling when used with the Vapor Sorbent Ticket, automated particulate sampling when used with the Particulate Collection Ticket, tickets can be pre-loaded entering into a hazardous material incident, all input functions (on/off, start/reset, set delay start time, collection duration, manual alarm (audio and visual) and mode setting (detection, collection, or test)), and output functions (device status, test status, alarm status (agent type and concentration)) that are performed on the reader device 10 can be performed remotely via a communications port 26, a concentrator may be connected to the intake port to increase detection sensitivity, multiple samples of similar or dissimilar airborne entities may be processed simultaneously with the collection elements 10, multiple samples of similar airborne entities at different times throughout the sampling process may can be processed with the collection elements 10, multiple samples of dissimilar airborne entities at different times throughout the sampling process can be processed with the collection elements 10, and the reader device 10 may use a general purpose classification collection element 30, e.g., combination of nerve, blister, and blood, to trigger the use of another reader device 10 with more specific classification EMTs, e.g., VX, GA, GB, GD, GF, etc.

The functioning of the system may include the following steps when using the modified M256 tickets as the collection element: Turn on device (ON/OFF switch)→warming up (LCD or LED) with internal checks of temperature, CPU, memory, optical component check (detector elements, lights source, light path, and background scale check from zero to 100% scale, date, time and battery condition check→ready mode (LCD and/or LED)→select mode (detection or collection)→instructions to follow on LCD (large font and back lighting)→remove packaging containing collection element 30→pull and discard Lewisite Tab #1→rub both halves of the white paper detector tab #2 on the tablet or remove tab #2 (for Lewisite tablet reader version)→remove heater assembly→discard heater pads→remove protective strip→open reader device 10 cover→insert newly formed collection element 30 with tab #2 on the upper left {Cover will close automatically w/string; a notch cutout in the bottom right-hand corner is blocked out in the slot area 12 to prevent accidental mis-insertion→press "start/reset" button→sampling/collection with LCD indicating mm.ss (m=minutes digit; s=seconds digit) or LED and/or audio output, e.g., beeping→sampling/collection complete (LCD and/or LED and/or audio output e.g., long beep or sequence of very short beeps→detector status (LCD and/or LED and/or audio output different beeping pattern for no alarm mode and alarm mode/agent type)→remove collection element 30→press "start/reset" button (stops alarm if applicable and ensures that the collection element 30 is removed, so the operator does not accidentally run the procedure on a used collection element 30→ready mode (same as above, the operator can make another run or turn off the reader device 10).

The reader device 10 may include several other components. Collectively, the components of the reader device may include an operator input interface, an operator output interface, collection element 30 holder, optical cavity, air handling assembly, temperature control assembly 18, ampule breaking assembly, microprocessor 24/memory, I/O assembly, collection element 30 for detection and collection, collection element 30 holder (metal, plastic—decontaminatable), temperature control surface or heater (resistor coil, Peltier device), temperature sensor (thermocouple, thermistor), timing unit (digital counter), timing display for sampling time and delay time (LED, LCD, plasma, etc.), sample ready light for collection element 30 surface and liquid (LED), detector ready light for electronic warm up (LED), motor for air handler, blow unit (carbon vane, fan, squirrel cage), plumbing (tubing, plenum), light source such as monochromatic/ polychromatic w/filter, dispersing element such as prism or holographic grading (LED, incandescent lamp, electroluminescent panel), light source controller (on/off controlled), detector element (charged coupled device (CCD), photodiode), central processing unit (CPU) (integrated circuit, separate logic circuit), input/output (I/O) ports (IEEE xxxx (FireWire), serial, parallel, universal serial bus (UBS), small computer serial interface (SCSI) type I-V), Global Positioning System (GPS) (differential, phased array, selectable availability (SA) mode, P-code), Global Positioning System interface, cellular phone interface (analog, digital, cellular digital packet data), power supply unit (AC/DC—international voltages 110V/220V, standard batteries/rechargeable, solar panel), solar panel, audio alarm (diaphragm speaker, solid state speaker—piezoelectric), visual alarm (LED, strobe—gas element, incandescent, fluorescent), audio alarm control unit (variable output patterns—pulse duration/pause duration), visual alarm control unit (variable output patterns—pulse duration/pause duration), ampules breaking unit (motor cam drive, spring load hammer (mechanical or solenoid pull back) with release, screw drive, hydraulic piston, pneumatic piston), battery checker unit (voltage meter—operation amplifier, analog-to-digital (A/D)—operation amplifier, comparitor), detector circuit unit (operation amplifier, analog-to-digital (A/D)—operation amplifier, comparitor), concentrator unit with heating and cooling on sample air intake and sampling unit on sample air exhaust (adsorbent—solid stationary phase charcoal, molecular sieves—liquid stationary phase) in addition to other components that facilitate the collection and detection of airborne hazardous materials.

The microprocessor 24 of the reader device 10 automates the collection and detection processing of hazardous material with the collection element 30, and initiates an indicator means 22, such as an audio and/or visual alarm/warning and status reporting component when a given set of parameters of the microprocessor 24 are reached. With the automation of these and other functions, the operator is available to perform other duties to contend with the hazard, e.g., mitigating the hazard, assisting other personnel in search and rescue, equipment and instrumentation setup, situational reporting, and other like tasks, and/or aiding in the coordination of military unit deployment. Also with the automation of the reader device, critical response time at an emergency hazardous material incident is maximized by increasing the number of trained personnel available to perform other tasks by implementing automated processes. Automation reduces operator participation from approximately 15 minutes down to 1 minute to obtain the desired results, and reduces the training required of the operators. Additionally, the time to initiate the sampling process is reduced and decreases the time to detection. An operator in donned PPE or MOPP gear does not manually conduct the many detailed manipulations in a chronological sequence that was previously required. Complex instructions are reduced to simpler initiation steps, reducing operator error, and difficult procedure manipulations are eliminated. Physical environmental factors, such as temperature and ultraviolet radiation, are controlled to ensure more accurate testing results, with ultraviolet radiation exposure to the collection element 30 eliminated and the temperature around the collection element 30 controlled, improving reliability and reproducibility. Variations in color and intensity interpretation are removed from the analysis of the testing procedures. The heating process to dry out the blister agent detector area on the collection element 30 is more precisely controlled, with shorter evaporation times and improved detection times resulting in improved reliability and reproducibility. Additionally, safety is increased with the removal of the limited temperature control from an exothermic heater on a ticket. The reader device 10 has the ability to start automatically at some operator's relative or absolute specified time. This allows multiple reader devices 10 in the same local environment to sample over an extended time duration.

The reader device 10 also is capable of remotely controlling the automated process and remotely obtaining all of the same data to which the local operator has access, via the onboard input/output characteristics of the reader device 10. All input functions, such as on/off, start/reset, set delay start time, collection duration, manual audio or visual alarm, and mode setting, such as maintenance, detection, collection, or test, can be performed on the reader device 10 remotely via a communications port 26 that is capable of receiving instructions and sending detection information with an external station. The communications port 26 may be connected with a fiber optical connection, remote signaling, cable and/or other similar data transmission conduit. Additionally, output functions, such as device status, test status, and alarm status of agent type and concentration can be obtain from the reader device 10 remotely via the same or a different communications port 26. This feature reduces the responsibilities of the operator, who may be an emergency responder with limited air supply in protective gear. Additionally, real-time data and information from the reader device 10 is available to other operators in the area, and/or more remote personnel, such as at a command post, who can integrate and coordinate information and situation responses. The reader device 30 may be connected to other reader devices 30 to share information, especially in combination with the Global Positioning System (GPS) or other location system. As such, a comprehensive approach to an warfare agent threat is available using a more comprehensive knowledge of the location of the threat in relation to the location of the response personnel, and optimizing trained personnel resources. With a comprehensive response, hot zones can be maintained and reestablished quickly, with a conservation of resources. Individual units may be alerted to a warfare agent threat, even if that unit does not detect the warfare agent threat, from a remote command site monitoring an area.

EXAMPLE

A collection element for detecting an airborne nerve agent is inserted into a reading device, and the reading device with the inserted collection element are transported to an area of possible contamination. The "on/off" button on the reader device is pushed, and the initiator key on the collection element keys the microprocessor to regulate the temperature of the area adjacent to the collection element within the reader device and to activate the crushing mechanism to crush ampules attached to the collection element to release a first chemical reagent. The microprocessor then initiates the micro-pump to collect and concentrate an airborne sample on the collection element. After a given amount of time, the microprocessor activates the crushing mechanism to crush ampules attached to the collection element to release a second chemical reagent, and initiates a time-interval color reading of the collection element by the diode reading component. With the color reading indicating the presence of nerve agent in the sample, the microprocessor activates an audio and visual alarm to warn persons in the area of the presence of the nerve agent. As further testing is done, the microprocessor breaks a plurality of ampules over a timed sequence to further provide monitoring for increased amounts of contaminant in the environment. The reader device is joined to other readers to form a detection net, using the communications port, and a relay is used to map the detection of nerve agents by concentration in a wide area with a global positioning system.

It should be understood that the foregoing summary, detailed description, drawing, and examples of the present invention are not intended to be limiting, but are only exemplary of the inventive features which are defined in the claims.

What is claimed is:

1. An airborne hazardous material reader device, comprising:

a body forming a slot area capable of receiving a collection element therein;

a crushing mechanism located within said slot area capable of breaking a plurality of ampules attached to said collection element sufficient to release chemical testing reagents therefrom;

a micro-pump positioned proximate to said slot area and capable of moving airborne hazardous material into said slot area;

means for regulating the temperature within said slot area;

a diode reading component incorporated within said body, the diode reading component capable of distinguishing color changes on said received collection element;

an indicator alarm means effective to indicate the presence of a hazardous material when said diode reading component distinguishes color changes; and, a microprocessor incorporated into said body, said microprocessor: monitoring and controlling said temperature regulation means to control the temperature within said slot area; controlling said diode reading component to evaluate said collection element's physical condition by checking for white, clean detector areas to ensure that said collection element has not been contaminated with dirt; activating said crushing mechanism in an appropriate sequence and time to crush said ampules; controlling said micro-pump to regulate the airflow over said collection element; and initiating a time-interval color reading of said collection element by said diode reading component and monitoring the frequency and intensity of color changes detected by said diode reading component; and activating the indicator alarm means in relation to said color reading.

2. The device of claim 1, further comprising a communications port capable of receiving instructions from, and sending detection information to, an external station.

3. The device of claim 2, wherein the communications port comprises a relay system selected from the group consisting of fiber optical connection, remote signaling, and cable.

4. The device of claim 1, further comprising a UV protection component effective to shield said received collection element.

5. The device of claim 1, wherein the indicator means comprises an alarm selected from the group consisting of audio and visual alarms.

6. The device of claim 1, wherein the diode reading component is capable of distinguishing at least three colors for photometric assessment.

7. The device of claim 1, wherein the indicator alarm means is capable of being read remotely.

8. The device of claim 1, wherein said collection element, comprises:

a porous substrate capable of absorbing airborne contaminants thereon;

said plurality of ampules containing chemical reagent material attached to the porous substrate and capable of breakage that releases the chemical reagent material onto the porous substrate; and, an initiator key enabling said reader device to identify a process to be conducted by said reader device to analyze said collection element; and wherein said collection element is capable of insertion into said reader device.

9. The collection element of claim 8, wherein the collection element comprises a predetermined selection of chemical reagent material capable of testing for a plurality of contaminants.

10. The collection element of claim 8, wherein the chemical reagent material comprises preservative chemicals.

11. The collection element of claim 10, wherein the preservative chemicals are selected from the group consisting of buffering agents and antioxidant agents.

12. The collection element of claim 8, wherein said initiator key comprises an initiator selected from the group consisting of optical character readers, color key swatch, alphanumeric indicators, and bar codes.

13. A method for detection of airborne hazardous material, comprising the steps of:

(a) providing an airborne hazardous material reader device, comprising a body forming a slot area capable of receiving a collection element therein;

a crushing mechanism located within said slot area capable of breaking a plurality of ampules attached to said collection element sufficient to release chemical testing reagents therefrom;

a micro-pump positioned proximate to said slot area and capable of moving airborne hazardous material into said slot area;

means for regulating the temperature within said slot area;

a diode reading component incorporated within said body, the diode reading component capable of distinguishing color changes on said received collection element;

an indicator alarm means effective to indicate the presence of a hazardous material when said diode reading component distinguishes color changes; and, a microprocessor incorporated into said body, said microprocessor: monitoring and controlling said temperature regulation means to control the temperature within said slot area; controlling said diode reading component to evaluate said collection element's physical condition by checking for white, clean detector areas to ensure that said collection element has not been contaminated with dirt;

activating said crushing mechanism in an appropriate sequence and time to crush said ampules; controlling said micro-pump to regulate the airflow over said collection element; and initiating a time-interval color reading of said collection element by said diode reading component and monitoring the frequency and intensity of color changes detected by said diode reading component; and activating the indicator alarm means in relation to said color reading;

(b) placing said collection element into said reader device;

(c) transporting said reader device containing said collection element to an area of possible contamination; and (d) activating said device.

14. The method of claim 13, further comprising the step of connecting said reader device with other reader devices to form a detection network.

15. The method of claim 13, further comprising the step of coordinating the detection of a hazardous material by said reader device with a global positioning system.

16. The method of claim 13, wherein said collection element includes ampules containing chemical reagent material attached to a porous substrate and capable of breakage so that said reagents are released onto said porous substrate, and wherein said ampules are broken over a timed sequence wherein the latter broken ampules provide detection of an increased amount of contaminant.

* * * * *